United States Patent
Yamada et al.

(10) Patent No.: US 9,212,065 B2
(45) Date of Patent: Dec. 15, 2015

(54) ZIRCONIA SINTERED BODY, ZIRCONIA COMPOSITION AND ZIRCONIA CALCINED BODY, AND DENTAL PROSTHESIS

(71) Applicant: Kuraray Noritake Dental Inc., Okayama (JP)

(72) Inventors: Yoshihisa Yamada, Aichi (JP); Atsushi Matsumoto, Aichi (JP); Yoshihisa Ito, Aichi (JP)

(73) Assignee: Kuraray Noritake Dental Inc., Kurashiki-shi (JP)

( * ) Notice: Subject to any disclaimer, the term of this patent is extended or adjusted under 35 U.S.C. 154(b) by 86 days.

(21) Appl. No.: 14/206,014

(22) Filed: Mar. 12, 2014

(65) Prior Publication Data
US 2014/0328746 A1 Nov. 6, 2014

(30) Foreign Application Priority Data

May 2, 2013 (JP) ................................. 2013-097058

(51) Int. Cl.
*C04B 35/486* (2006.01)
*A61C 13/00* (2006.01)
(Continued)

(52) U.S. Cl.
CPC ............ *C01G 25/02* (2013.01); *A61C 13/0022* (2013.01); *C04B 35/486* (2013.01); *C04B 35/62655* (2013.01); *A61C 8/0012* (2013.01); *A61C 13/083* (2013.01); *C04B 2235/3218* (2013.01); *C04B 2235/3224* (2013.01); *C04B 2235/3225* (2013.01); *C04B 2235/3232* (2013.01); *C04B 2235/3241* (2013.01); *C04B 2235/3272* (2013.01); *C04B 2235/5445* (2013.01); *C04B 2235/6026* (2013.01); *C04B 2235/612* (2013.01); *C04B 2235/656* (2013.01);
(Continued)

(58) Field of Classification Search
CPC .. C04B 35/486; A61C 13/083; A61C 8/0012; A61C 8/0013; Y10T 428/24942
See application file for complete search history.

(56) References Cited

U.S. PATENT DOCUMENTS

| | | | | |
|---|---|---|---|---|
| 4,742,030 A | * | 5/1988 | Masaki | C04B 35/486 423/608 |
| 7,981,531 B2 | * | 7/2011 | Rheinberger | A61C 13/0004 428/454 |

(Continued)

FOREIGN PATENT DOCUMENTS

JP 2008068079 3/2008

OTHER PUBLICATIONS

Katana Zirconia Materials, Koeln International Dental Show, 2013, Koeln Messe hall (Koeln, Germany).

*Primary Examiner* — Karl Group
(74) *Attorney, Agent, or Firm* — Oblon, McClelland, Maier & Neustadt, L.L.P.

(57) ABSTRACT

Zirconia sintered body having similar appearance to natural tooth. On straight line extending in first direction from one end to the other end of zirconia sintered body, when chromaticity (L*, a*, b*) by a L*a*b* colorimetric system of first point positioned in section from the one end to 25% of the whole length is (L1, a1, b1) and chromaticity (L*, a*, b*) by L*a*b* colorimetric system of second point positioned in section from the other end to 25% of whole length is (L2, a2, b2), L1 ranges from 58.0 to 76.0, a1 ranges from −1.6 to 7.6, b1 ranges from 5.5 to 26.3, L2 ranges from 71.8 to 84.2, a2 ranges from −2.1 to 1.8, b2 ranges from 1.9 to 16.0, L1<L2, a1>a2, b1>b2, and tendency to increase or decrease chromaticity by the L*a*b* colorimetric system from first point to second point does not change.

15 Claims, 1 Drawing Sheet

(51) Int. Cl.
  *C01G 25/02* (2006.01)
  *C04B 35/626* (2006.01)
  *A61C 8/00* (2006.01)
  *A61C 13/083* (2006.01)

(52) U.S. Cl.
  CPC ....... *C04B 2235/76* (2013.01); *C04B 2235/765* (2013.01); *C04B 2235/96* (2013.01); *C04B 2235/9661* (2013.01)

(56) References Cited

U.S. PATENT DOCUMENTS

| | | | | |
|---|---|---|---|---|
| 8,173,562 B2* | 5/2012 | Holand | .................... | A61C 5/10 264/20 |
| 8,796,166 B2* | 8/2014 | Holand | .................... | A61C 5/10 106/35 |
| 8,936,848 B2* | 1/2015 | Jung | ........................ | B32B 18/00 428/211.1 |
| 2007/0292597 A1* | 12/2007 | Ritzberger | ............... | A61C 5/10 427/2.29 |
| 2008/0064011 A1 | 3/2008 | Rheinberger et al. | | |
| 2008/0303181 A1* | 12/2008 | Holand | .................... | A61C 5/10 264/16 |
| 2011/0236855 A1 | 9/2011 | Rheinberger et al. | | |
| 2011/0236857 A1 | 9/2011 | Rheinberger et al. | | |
| 2011/0319254 A1* | 12/2011 | Ritzberger | ............... | A61C 5/10 501/134 |

* cited by examiner

ZIRCONIA SINTERED BODY, ZIRCONIA COMPOSITION AND ZIRCONIA CALCINED BODY, AND DENTAL PROSTHESIS

REFERENCE TO RELATED APPLICATION

The present disclosure is based upon and claims the benefit of the priority of Japanese patent application No. 2013-097058 filed on May 2, 2013, the disclosure of which is incorporated herein in its entirety by reference thereto.

TECHNICAL FIELD

The present disclosure relates to a zirconia sintered body. The present disclosure also relates to a composition and a calcined body for manufacturing the zirconia sintered body (a precursor body for sintering zirconia sintered body is generally termed herein as "calcined body"). In addition, the present disclosure relates to a dental prosthesis (prosthetic material) having the zirconia sintered body.

BACKGROUND

In dental treatment, a prosthetic tooth is used as a substitute for a natural tooth. The same appearance as the natural tooth is required for this prosthetic tooth.

Patent literature 1 discloses a multicolored shaped body having layers arranged on top one another for producing dental restorations. The shaped body described in Patent literature 1 comprises at least two successive and differently colored main layers and (b) at least two differently colored intermediate layers between the at least two successive and differently colored main layers, and a change in color between the intermediate layers takes place in a direction which is reverse to a direction of color change between the main layers.

Patent Literature (PTL)

[PTL 1] JP Patent Kokai Publication No. JP2008-68079A

SUMMARY

The entire disclosure of the above mentioned Patent Literature is incorporated herein by reference thereto. The following analyses are given in view of the present disclosure.

Zirconium oxide (IV) ($ZrO_2$) (hereinafter, called "zirconia") is used as a dental material for manufacturing the prosthetic tooth because zirconia has a high strength and also a whitish color tone. The natural tooth has a color change such that a color becomes deep from a root side of the tooth toward a crown side of the tooth. Accordingly, it is considered to laminate several layers having different colors such as the shaped body described in Patent literature 1, as a method for forming the same appearance as a natural tooth with zirconia.

As to the shaped body described in Patent literature 1, however, two intermediate layers intervene between adjacent main layers. A color change direction of the two intermediate layers is reverse to a color change direction of the natural tooth. For this reason, the same color change as the natural tooth can not be unreproducible for the shaped body described in Patent literature 1.

According to a first aspect of the present disclosure, there is provided a zirconia sintered body, wherein, on a straight line extending in a first direction from one end to the other end, when a chromaticity ($L^*$, $a^*$, $b^*$) by a $L^*a^*b^*$ colorimetric system of a first point positioned in a section from the one end to 25% of a whole length is ($L1$, $a1$, $b1$) and a chromaticity ($L^*$, $a^*$, $b^*$) by the $L^*a^*b^*$ colorimetric system of a second point positioned in a section from the other end to 25% of the whole length is ($L2$, $a2$, $b2$), L1 ranges from 58.0 to 76.0, a1 ranges from −1.6 to 7.6, b1 is a range from 5.5 to 26.3, L2 ranges from 71.8 to 84.2, a2 ranges from −2.1 to 1.8, b2 ranges from 1.9 to 16.0, L1<L2, a1>a2, b1>b2, and a tendency to increase or decrease the chromaticity by the $L^*a^*b^*$ colorimetric system from the first point to the second point does not change.

According to a second aspect of the present disclosure, there is provided a zirconia sintered body, color changes in a first direction from one end toward the other end, and a tendency to increase or decrease the chromaticity by the $L^*a^*b^*$ colorimetric system on a straight line from such one end to the other end does not change.

According to a third aspect of the present disclosure, there is provided a calcined body for manufacturing a zirconia sintered body, the calcined body is turned to the zirconia sintered body of the above first aspect or the second aspect by sintering the calcined body at a temperature ranging from 1400 degrees Celsius to 1600 degrees Celsius.

According to a fourth aspect of the present disclosure, there is provided a composition for manufacturing a zirconia sintered body, the composition is turned to the zirconia sintered body of the above first aspect or the second aspect by sintering the composition at a temperature ranging from 1400 degrees Celsius to 1600 degrees Celsius.

According to a fifth aspect of the present disclosure, there is provided a composition for manufacturing a zirconia sintered body, the composition is turned to the calcined body of the above third aspect by burning the composition at a temperature ranging from 800 degrees Celsius to 1200 degrees Celsius.

According to a sixth aspect, there is provided a sintered dental prosthesis after machining (including milling, cutting, turning, and/or grinding, generally termed as "machining" herein corresponding to Japanese term "Sessaku-Kako") the calcined body of the third aspect.

The present disclosure has at least one of the following effects.

According to the zirconia sintered body of the present disclosure, an appearance like a natural tooth is realizable.

According to the composition and the calcined body of the present disclosure, the zirconia sintered body as described above is obtainable.

MODES

Figure 1:
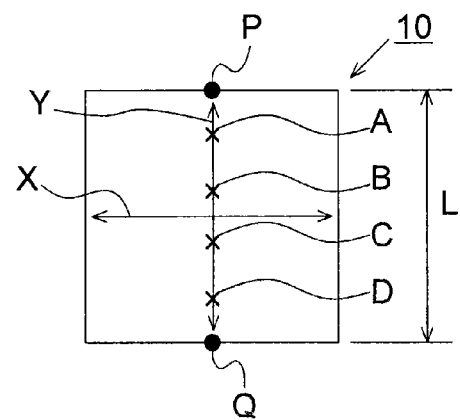
FIG. 1 is a schematic diagram of a zirconia sintered body.

Preferred modes of the above respective aspects are described as follows.

According to a preferred mode of the first aspect, on the straight line connecting the first point and the second point, there is no section where the $L^*$ value decreases by 1 or more from the first point toward the second point, there is no section where the $a^*$ value increases by 1 or more from the first point toward the second point, and there is no section where the $b^*$ value increases by 1 or more from the first point toward the second point.

According to a preferred mode of the first aspect, on the straight line connecting from the first point to the second point, when a chromaticity (L*, a*, b*) by the L*a*b* colorimetric system of a third point between the first point and the second point is (L3, a3, b3), L3 ranges from 65.9 to 80.5, a3 ranges from −1.8 to 5.5, b3 ranges from 4.8 to 20.7, L1<L3<L2, a1>a3>a2, and b1>b3>b2.

According to a preferred mode of the first aspect, on the straight line connecting from the first point to the second point, when a chromaticity (L*, a*, b*) by the L*a*b* colorimetric system of a forth point between the third point and the second point is (L4, a4, b4), L4 ranges from 69.1 to 82.3, a4 ranges from −2.1 to 1.4, b4 ranges from 3.5 to 16.2, L1<L3<L4<L2, a1>a3>a4>a2, and b1>b3>b4>b2.

According to a preferred mode of the first aspect, the third point is placed at a distance of 45% of the whole length from one end. The fourth point is placed at a distance of 55% of the whole length from one end.

According to a preferred mode of the above first aspect, in the first point, the third point, the fourth point and the second point, when a difference in the L* value between adjacent two points is $\Delta L^*$, a difference in the a* value between adjacent two points is $\Delta a^*$, a difference in the b* value between adjacent two points is $\Delta b^*$ and $\Delta E^*ab$ is calculated by the following formula, $\Delta E^*ab$ between the first point and the third point ranges from 3.7 to 14.3, $\Delta E^*ab$ between the third point and the fourth point ranges from 1.8 to 10.5, and $\Delta E^*ab$ between the fourth point and the second point ranges from 1.0 to 4.8.

$$\Delta E^* ab = \sqrt{(\Delta L^*)^2 + (\Delta a^*)^2 + (\Delta b^*)^2}$$

According to a preferred mode of the above first aspect, on the straight line connecting from the first point to the second point, when a chromaticity (L*, a*, b*) by th L*a*b* colorimetric system of the third point between the first point and the second point is (L3, a3, b3), L3 ranges from 69.1 to 82.3, a3 ranges from −2.1 to 1.4, b3 ranges from 3.5 to 16.2, L1<L3<L2, a1>a3>a2, and b1>b3>b2.

According to a preferred mode of the above second aspect, on a straight line connecting one end and the other end, there are a tendency of increasing the L* value and a tendency of decreasing the a* value and the b* value, from the first point toward the second point.

According to a preferred mode of the above first aspect and the above second aspect, a distance from one end to the other end ranges from 5 mm to 18 mm.

According to a preferred mode of the above first aspect and the above second aspect, there is no change of a color along a second direction perpendicular to the first direction.

According to a preferred mode of the above first aspect and the above second aspect, as to two points on a straight line extending in the second direction, when a difference in the L* value between two points is $\Delta L^*$, a difference in the a* value between two points is $\Delta a^*$, a difference in the b* value between two points is $\Delta b^*$ and $\Delta E^*ab$ is calculated by the above formula, $\Delta E^*ab$ is less than 1.

According to a preferred mode of the above first aspect and the above second aspect, a value of flexural strength measured in conformity with JISR1601 is 1000 MPa or more.

According to a preferred mode of the above first aspect and the above second aspect, a value of fracture toughness measured in conformity with JISR1607 is 3.5 MPa·m$^{1/2}$ or more.

According to a preferred mode of the above first aspect and the above second aspect, in an X-ray diffraction pattern of the zirconia sintered body after applying a hydrothermal test at a temperature of 180 degrees Celsius and a pressure of 1 MPa for 5 hours, a peak ratio is 1 or less, the peak ratio being a ratio of a height of a peak existing near a position around 28° of 2θ where a monoclinic [11-1] peak appears to a height of a peak existing near a position around 30° of 2θ where a tetragonal [111] peak appears.

According to a preferred mode of the above sixth aspect, a machining is performed with a CAD/CAM system.

In the present disclosure, for example, if the zirconia sintered body has a tooth crown shape, it is preferred that the above "one end" and "the other end" indicate one point of an edge part of a cut side and one point of an edge part of a root side. Such one point may be a point on an edge surface or a point on a cross-sectional surface. A point placed within a section from one end or the other end to 25% of the whole length means a point (position) away from one end or the other end by a distance corresponding to 10% of tooth crown height, for example.

In the case where the zirconia sintered body has a disc shape and a hexahedral shape such as a rectangular parallelepiped, it is preferred that the above "one end" and "the other end" indicate a point on an upper surface and a lower surface (bottom). Such one point may be a point on an edge surface or a point on a cross-sectional surface. A point placed within a section from one end or the other end to 25% of the whole length means a point (position) away from one end or the other end by a distance corresponding to 10% of a thickness of the hexahedron or the disc, for example.

In the present disclosure, "a first direction from one end toward the other end" means a direction of a change in color. For example, it is preferred that the first direction is a direction of laminating powders in a manufacturing method as described below. For example, in the case where the zirconia sintered body has tooth crown shape, it is preferred that the first direction is a direction connecting the cut edge side and the root side.

The zirconia sintered body of the present disclosure will be explained. The zirconia sintered body of the present disclosure is a sintered body in which partially-stabilized zirconia crystal particles are mainly (as a main component) sintered, and has the partially-stabilized zirconia as a matrix phase. In the zirconia sintered body of the present disclosure, a main crystal phase of the zirconia is a tetragonal system. (In a state before applying a hydrothermal test, described below) it is preferred that a monoclinic crystal is not substantially included in the zirconia sintered body.

The zirconia sintered body of the present disclosure includes not only a sintered body in which shaped zirconia particles are sintered under atmospheric pressure or without applying additional pressure but also a sintered body densified by a high temperature and pressure treatment, for example, a HIP (Hot Isostatic Pressing) treatment and the like.

The zirconia sintered body of the present disclosure includes zirconia and a stabilizing agent (s) thereof. The stabilizing agent(s) inhibits a phase transition from the tetragonal system to the monoclinic system. According to the inhibition of the phase transition, strength, durability and dimension precision can be improved. Oxides such as calcium oxide (CaO), magnesium oxide (MgO), yttrium oxide ($Y_2O_3$) (hereinafter, called as "yttria"), cerium oxide ($CeO_2$) and the like may be given as an example of the stabilizing agent (s). It is preferred that an amount of the stabilizing agent(s) is present enough to partially stabilize the tetragonal system zirconia particles. If yttria is used as the stabilizing agent(s), for example, the content rate of yttria may be preferably 2.5 mol % to 5 mol %, more preferably 3 mol % to 4.5 mol %, and further more preferably 3.5 mol % to 4.5 mol % relative to the total mole of zirconia and yttria. If the content of the stabilizer (s) is increased too much, even if it can inhibit the phase transition, it decreases the flexural strength and the fracture toughness. On the other hand, if the content of the stabilizer(s) is too low, even if it can inhibit the lowering of the flexural strength and the fracture toughness, it is insufficient to inhibit progress of the phase transition. Meanwhile, a partially-stabilized tetragonal system zirconia to which the stabilizing agent (s) is added is called as a partially-stabilized zirconia (PSZ).

It is preferred that the zirconia sintered body of the present disclosure includes aluminum oxide ($Al_2O_3$: alumina). It is preferred that aluminum oxide is alpha-alumina. If aluminum oxide is included, the strength can be improved. It is preferred that a content rate of aluminum oxide in the zirconia sintered body is 0 mass % (not included) to 0.3 mass % to the total amount (weight) of zirconia and the stabilizing agent (s). If aluminum oxide is included more than 0.3 mass %, it decreases a translucency.

It is preferred that the zirconia sintered body of the present disclosure includes titanium oxide ($TiO_2$: titania). If titanium oxide is included, grain growth can be facilitated. It is preferred that a content rate of titanium oxide in the zirconia sintered body is from 0 mass % (not included) to 0.6 mass % relative to the total amount of zirconia and the stabilizing agent (s). If titanium oxide is included more than 0.6 mass %, it decreases the strength.

In the zirconia sintered body of the present disclosure, it is preferred that a content rate of silicon dioxide ($SiO_2$: silica) is 0.1 mass % or less to the total amount of zirconia and the stabilizing agent (s), and that the zirconia sintered body does not contain silicon oxide substantially. This is a reason why the transparency of the zirconia sintered body falls if silicon oxide is included. Here, the phrase "not contain substantially" indicates meaning of inclusion within a range which does not have an influence particularly on characteristic and property of the present disclosure and preferably the meaning of not containing (silicon oxide) more than an impurity level, and it does not necessarily mean an inclusion less than a detection limit.

The zirconia sintered body of the present disclosure may include a coloring agent(s). Chromium oxide ($Cr_2O_3$), erbium oxide ($Er_2O_3$), iron oxide ($Fe_2O_3$), praseodymium oxide ($Pr_6O_{11}$) and the like may be given as an example of the coloring agent (s). These coloring agents may be used in a combination thereof. A content of coloring agent(s) differs partially.

For example, in the case where the zirconia sintered body used as dental material includes chromium oxide, it is preferred that a partial content of chromium oxide in a region containing chromic oxide is 0.001 mass % or less to the total amount of zirconia and the stabilizing agent. In the case where the zirconia sintered body used as the dental material includes erbium oxide, it is preferred that a partial content of erbium oxide in a region containing erbium oxide is 2 mass % or less to the total amount of zirconia and the stabilizing agent. For example, in the case where the zirconia sintered body used as the dental material includes iron oxide, it is preferred that a partial content of iron oxide in a region containing iron oxide is 0.1 mass % or less to the total amount of zirconia and the stabilizing agent. For example, in the case where the zirconia sintered body used as the dental material includes praseodymium oxide, it is preferred that a partial content of praseodymium oxide in a region containing praseodymium oxide is 0.1 mass % or less to the total amount of zirconia and the stabilizing agent.

After making the zirconia sintered body, in an X-ray diffraction pattern, which is measured with CuKα rays, of a zirconia sintered body in a state before treated with a hydrothermal test (described in the below) as a degradation acceleration test, it is preferred that a ratio of a height of a peak (hereinafter, called as "second peak") existing near a position around 28° of 2θ where a [11-1] peak of the monoclinic system appears to a height of a peak (hereinafter, called as "first peak") existing near a position around 30° of 2θ where a [111] peak of the tetragonal system appears (that is, "the height of the second peak"/"the height of the first peak"; referred to as "the peak ratio of the monoclinic system" hereinafter) is 0.1 or less and preferably 0.05 or less.

In the zirconia sintered body of the present disclosure, the phase transition from the tetragonal system to the monoclinic system is inhibited although the hydrothermal test is applied to the zirconia sintered body. For example, when applying the hydrothermal test at a temperature of 180 degrees Celsius and a pressure of 1 MPa for 5 hours to the zirconia sintered body of the present disclosure, in an X-ray diffraction pattern, which is measured with CuKα rays, of a surface of a zirconia sintered body after hydrothermal test, it is preferred that the peak ratio of the monoclinic system is 1 or less, preferably 0.8 or less, more preferably 0.7 or less, and further more preferably 0.6 or less.

In the description, the term "hydrothermal treatment test" is a test conforming to ISO13356, with the proviso as follows. That is, although a condition provided in ISO13356 is "134 degrees Celsius, 0.2 MPa, 5 hours", a corresponding condition of the acceleration test in the prevent disclosure is changed to "180 degrees Celsius, 1 MPa" to make the condition of the test severer, and a test time is suitably determined corresponding to a purpose. Hereinafter, the hydrothermal treatment test is also expressed as "low-temperature degradation acceleration test" or "hydrothermal degradation test".

In the zirconia sintered body of the present disclosure, it is preferred that a value of fracture toughness measured in conformity with JISR1607 is 3.5 MPa·m$^{1/2}$ or more, preferably 3.8 MPa·m$^{1/2}$ or more, more preferably 4 MPa·m$^{1/2}$ or more, and further more preferably 4.2 MPa·m$^{1/2}$ or more. In addition, these values are values in a state where the hydrothermal treatment is not applied. In addition, in the test piece, a boundary in case where compositions having different components are laminated extends along a direction of applying the load (along a minimum area direction) and traverses the test piece. The boundary is positioned at the center (middle of longitudinal direction) of the test piece.

Figure 2:
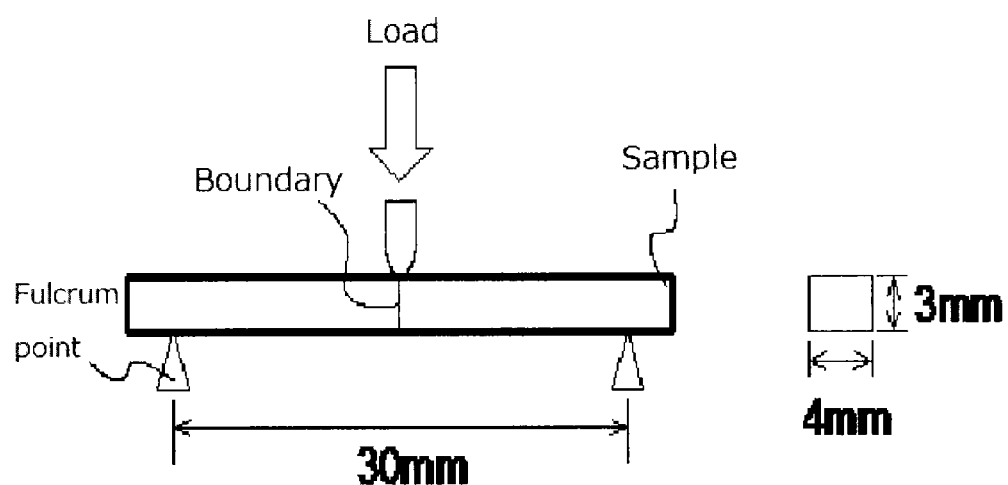
FIG. 2 is a schematic diagram for explaining a method for a three-point bending test.

In the zirconia sintered body of the present disclosure, it is preferred that a value of flexural strength measured in conformity with JISR1601 is 1000 MPa or more, preferably 1050 MPa or more. In addition, these values are values in a state where the hydrothermal treatment is not applied. In FIG. 2, a schematic diagram of a three-point bending test is shown. In the test piece, a boundary in case where compositions having different components are laminated extends along a direction applying the load (along a minimum area direction) and traverses the test piece. The boundary is positioned at the center (middle of longitudinal direction) of the test piece. A load point of the three-point bending test is consistent with the position of the concerned boundary.

In the zirconia sintered body of the present disclosure, it is preferred that the above-mentioned value is satisfied with respect to all of the peak ratio of the monoclinic system after the hydrothermal test, the flexural strength and the fracture toughness. For example, in the zirconia sintered body of the present disclosure, it is preferred that the peak ratio of the monoclinic system after hydrothermal test is 1 or less, the fracture toughness is 3.5 MPa·m$^{1/2}$ or more and the flexural strength is 1000 MPa or more. In the zirconia sintered body of the present disclosure, it is further preferred that the peak ratio of the monoclinic system after the hydrothermal test is 0.6 or less, the fracture toughness is 4 MPa·m$^{1/2}$ or more and the flexural strength is 1000 MPa or more.

In the zirconia sintered body of the present disclosure, there is a direction where a color does not change substantially. In FIG. 1, a schematic diagram of a zirconia sintered body is shown. For example, in a zirconia sintered body 10 shown in FIG. 1, it is preferred that a color does not change substantially in a first direction X. For example, between any two points on a straight line extending in the first direction X, when differences in L* value, a* value and b* value according to a L*a*b* colorimetric system (JISZ8729) are set as ΔL*, Δa*, and Δb*, respectively and ΔE*ab is calculated according to the following formula, it is preferred that ΔE*ab is less than 1, and more preferably less than 0.5.

$$\Delta E^*ab = \sqrt{(\Delta L^*)^2 + (\Delta a^*)^2 + (\Delta b^*)^2}$$

In addition, in the zirconia sintered body of the present disclosure, color changes from one end to the other end, the one end and the other end connecting both edges. In the zirconia sintered body 10 shown in FIG. 1, on a straight line extending along a second direction Y from one end P to the other end Q, it is preferred that a tendency of increasing or a tendency of decreasing of the L* value, a* value and b* value does not change in an opposite direction. That is, in the case where there is a tendency of increasing the L* value on the straight line from one end P to the other end Q, it is preferred that there is no section that the L* value substantially decreases. For example, in the case where there is a tendency of increasing the L* value on the straight line from one end P to the other end Q, it is preferred that there is no section that the L* value decreases by 1 or more, and more preferably there is no section that the L* value decreases by 0.5 or more. In the case where there is a tendency of decreasing the a* value on the straight line from one end P to the other end Q, it is preferred that there is no section that the a* value increases substantially. For example, in the case where there is a tendency of decreasing the a* value on the straight line from one end P to the other end Q, it is preferred that there is no section that the a* value increases by 1 or more, and more preferably there is no section that the a* value increases by 0.5 or more. In addition, in the case where there is a tendency of decreasing the b* value on the straight line from one end P to the other end Q, it is preferred that there is no section that the b* value increases substantially. For example, in the case where there is a tendency of decreasing the b* value on the straight line from one end P to the other end Q, it is preferred that there is no section that the b* value increases by 1 or more, and more preferably there is no section that the b* value increases by 0.5 or more.

In the case where the change in color of the zirconia sintered body 10 has a tendency of increasing the L* value from one end P to the other end Q, it is preferred that there is a tendency of decreasing of the a* value and the b* value. For example, the color is changed from light-yellow color, light orangey color or light-brownish color to white color, in a direction from one end P to the other end Q.

In FIG. 1, points on a straight line connecting from one end P to the other end Q are referred to as a first point A, a second point B, a third point C and a fourth point D in this order from the one end P side. It is preferred that the first point A is placed in a section from one end to, 25% to 45% of a length between one end P and other end Q (hereinafter, called as "whole length"). It is preferred that the second point B is placed in a section from a point away from one end P by 30% of the whole length to 70% of the whole length from one end P. It is preferred that the fourth point D is placed in a section from the other end Q to 25% to 45% of the whole length. It is preferred that the third point C is placed in a section from a point away from the other point Q by 30% of the whole length to 70% the whole length from the other end Q.

The chromaticities (L*, a*, b*) of the zirconia sintered body 10 by the L*a*b* colorimetric system (JISZ8729) for the first point A, the second point B, the third point C and the fourth point D are given as (L1, a1, b1), (L2, a2, b3), (L3, a3, b3) and (L4, a4, b4), respectively. At this time, it is preferred that the following magnitude correlation is established. In addition, a chromaticity of each point can be obtained by producing a zirconia sintered body which has composition independently corresponding to each point and measuring the chromaticity of the zirconia sintered body.

$$L1 < L2 < L3 < L4$$

$$a1 > a2 > a3 > a4$$

$$b1 > b2 > b3 > b4$$

In the case where the zirconia sintered body of the present disclosure is applied to the dental material, for example, it is preferred that L1 is included in a range from 58.0 to 76.0. It is preferred that L2 is included in a range from 65.9 to 80.5. It is preferred that L3 is included in a range from 69.1 to 82.3. It is preferred that L4 is included in a range from 71.8 to 84.2.

In the case where the zirconia sintered body of the present disclosure is applied to the dental material, for example, it is preferred that a1 is included in a range from −1.6 to 7.6. It is preferred that a2 is included in a range from −1.8 to 5.5. It is preferred that a3 is included in a range from −2.1 to 1.4. It is preferred that a4 is included in a range from −2.1 to 1.8.

In the case where the zirconia sintered body of the present disclosure is applied to the dental material, for example, it is preferred that b1 is a included in range from 5.5 to 26.3. It is preferred that b2 is included in a range from 4.8 to 20.7. It is preferred that b3 is included in a range from 3.5 to 16.2. It is preferred that b4 is included in a range from 1.9 to 16.0.

In the case where the zirconia sintered body of the present disclosure is applied to the dental material, it is preferred that L1 is included in a range from 60.9 to 72.5, a1 is included in a range from 0.2 to 5.9, b1 is included in a range from 11.5 to 24.9, L4 is included in a range from 72.2 to 79.2, a4 is included in a range from −1.2 to 1.7 and b4 is included in a range from 6.0 to 15.8. More preferably, L1 is included in a range from 63.8 to 68.9, a1 is included in a range from 2.0 to 4.1, b1 is included in a range from 17.5 to 23.4, L4 is included in a range from 72.5 to 74.1, a4 is included in a range from −0.2 to 1.6 and b4 is included in a range from 10.1 to 15.6. Accordingly, the zirconia sintered body can be adapted to an average color tone of a natural tooth.

A color difference between adjacent two points ΔE*ab can be expressed by the following formula. ΔL* is a difference in the L* value between adjacent two layers (for example, L1−L2). Δa* is a difference in the a* value between adjacent two layers (for example, a1−a2). Δb* is a difference in the b* value between adjacent two layers (for example, b1−b2). In the case where it is given as that a color difference between the first point A and the second point B is ΔE*ab1, a color difference between the second point B and the third point C is ΔE*ab2 and a color difference between the third point C and the fourth point D is ΔE*ab3 and there is the above relationship for the chromaticity of the first point A, the second point B, the third point C and the fourth point D, it is preferred that a relationship of ΔE*ab41>ΔE*ab2>ΔE*ab3 is established. For example, it is preferred that ΔE*ab1 is included in a range from 3.7 to 14.3. It is preferred that ΔE*ab2 is included in a range from 1.8 to 10.5. It is preferred that ΔE*ab3 is included in a range from 1.0 to 4.8. Accordingly, the same color change as the natural tooth can be reproduced.

$$\Delta E^*ab = \sqrt{(\Delta L^*)^2 + (\Delta a^*)^2 + (\Delta b^*)^2}$$

In the case where it is given that a color difference between the first point A and the fourth point D is ΔE*ab4 and there is the above relationship for the chromaticity of the first point A, the second point B, the third point C and the fourth point D, for example, it is preferred that ΔE*ab4 is 30 or less. It is preferred that a value which is obtained by subtracting the color difference ΔE*ab4 between the first point A and the fourth point D from the sum total of the color difference ΔE*ab1 between the first point A and the second point B, the color difference ΔE*ab2 between the second point B and the third point C and the color difference ΔE*ab3 between the third point C and the fourth point D is 1 or less. Accordingly, a natural color change can be expressed.

In the case where the chromaticity of the fourth point D is in the above range, it is preferred that an optical transmittance of a sample, which is measured in conformity with on JISK7361, is 27% or more, the sample being produced by making the zirconia sintered body with a single composition corresponding to the fourth point and processing the zirconia sintered body in mirror-like finishing on both sides, the sample having a thickness of 0.5 mm. In addition, in the case where the chromaticity of the fourth point A is in the above range, it is preferred that an optical transmittance of a sample, which is measured in conformity with on JISK7361, is 10% or more, the sample being produced by making the zirconia sintered body with a single composition corresponding to the first point, and processing the zirconia sintered body in mirror-like finishing on both sides, the sample having a thickness of 0.5 mm, is produced.

In the zirconia sintered body 10 of the present disclosure, it is preferred that a length L in the first direction Y satisfies at least a corresponding length to an exposed part of a natural tooth. For example, it is preferred that the length L of the zirconia sintered body 10 is between 5 mm and 18 mm.

Next, a composition and a calcined body for manufacturing the zirconia sintered body of the present disclosure will be explained. The composition and the calcined body of the zirconia sintered body are a precursor (an intermediate product) of the zirconia sintered body of the present disclosure. The calcined body is made by burning the composition at a temperature which is insufficient to sinter (i.e. calcine) the composition. In addition, the calcined body may include a shaped and processed product. For example, a dental prosthesis (for example, a crown shape) which is made by processing a calcined zirconia disk with a CAD/CAM (Computer-Aided Design/Computer-Aided Manufacturing) system may be also included in the calcined body.

The composition and the calcined body include zirconia crystal particles, a stabilizing agent(s) and titanium oxide. The composition may also include aluminum oxide. It is preferred that aluminum oxide is alpha-alumina.

It is preferred that an average particle size of zirconia powder (in a state of granulated powder) of the composition is 20 μm to 40 μm.

Oxides such as calcium oxide (CaO), magnesium oxide (MgO), yttria, cerium oxide ($CeO_2$) and the like are given as an example of the stabilizing agent (s) for the composition and the calcined body. It is preferred that the stabilizing agent(s) having an amount enough to partially stabilize the zirconia particles is added. If yttria is used as the stabilizing agent(s), for example, the content of yttria may be preferably 2.5 mol % to 4.5 mol %, more preferably 3 mol % to 4.5 mol %, and further more preferably 3.5 mol % to 4.5 mol % relative to the total mole of zirconium and yttria.

It is preferred that a content rate of aluminum oxide in each of the composition and the calcined body is from 0 mass % (not included) to 0.3 mass % to the total mass of the zirconia crystal particles and the stabilizing agent(s). This purpose is to enhance the strength of the zirconia sintered body. If more than 0.3 mass % of aluminum oxide is included, the translucency of the zirconia sintered body will be lowered.

It is preferred that a content rate of titanium oxide in each of the composition and the calcined body is from 0 mass % (not included) to 0.6 mass % to the total mass of the zirconia crystal particles and the stabilizing agent(s). This purpose is to promote grain growth of the zirconia crystal. If more than 0.6 mass % of titanium oxide is included, the strength of the zirconia sintered body will decrease.

In each of the composition and the calcined body of the present disclosure, it is preferred that a content rate of silicon oxide is 0.1 mass % or less to the total mass of the zirconia crystal particles and the stabilizing agent(s), and the composition and the calcined body do not contain silicon oxide ($SiO_2$: silica) substantially. This is a reason why the translucency of the zirconia sintered body falls if silicon oxide is included. The phrase "not contain substantially" indicates meaning of inclusion within a range which does not have an influence particularly on characteristic and property of the present disclosure and preferably the meaning of not containing (silicon oxide) more than an impurity level, and the phrase does not necessarily mean the inclusion less than a detection limit.

Each of the composition and the calcined body of the present disclosure includes a coloring agent(s). Chromium oxide ($Cr_2O_3$), erbium oxide ($Er_2O_3$), iron oxide ($Fe_2O_3$), praseodymium oxide ($Pr_6O_{11}$) and the like may be given as an example of the coloring agent(s). These coloring agents may be used in combination thereof. A content of coloring agent(s) differs partially.

For example, in a formed (shaped) composition and calcined body, in the case where a 25% to 45% region of the whole thickness from a lower end is referred to as a first layer; a 5% to 25% region of the whole thickness placed on the first layer is referred to as a second layer; a 5% to 25% region of the whole thickness placed on the second layer is referred to as a third layer; and a 25% to 45% region of the whole thickness between the third layer and the upper end is referred to as a fourth layer, it is preferred that a content rate of coloring agent(s) decreases from the first layer to the fourth layer.

For example, in the case where a sintered body manufactured from the composition and the calcined body is used as a dental material, erbium oxide and iron oxide can be added as the coloring agent(s). In this case, it is preferred in the first layer that a content rate of erbium oxide is from 0.33 mass % to 0.52 mass % and a content rate of iron oxide is from 0.05 mass % to 0.12 mass %, relative to the total mass of the zirconia and the stabilizing agent(s). It is preferred in the second layer that a content rate of erbium oxide is from 0.26 mass % to 0.45 mass % and a content rate of iron oxide is from 0.04 mass % to 0.11 mass %, relative to the total mass of the zirconia and the stabilizing agent(s). It is preferred in the third layer that a content rate of erbium oxide is from 0.05 mass % to 0.24 mass % and a content rate of iron oxide is from 0.012 mass % to 0.08 mass %, relative to the total mass of the zirconia and the stabilizing agent(s). It is preferred in the fourth layer that a content rate of erbium oxide is from 0 mass % to 0.17 mass % and a content rate of iron oxide is from 0 mass % to 0.07 mass %, relative to the total mass of the zirconia and the stabilizing agent(s). It is preferred that the content rates of erbium oxide and iron oxide decrease from the first layer to the fourth layer, in turn.

For example, in the case where the sintered body manufactured from the composition and the calcined body is used as the dental material, erbium oxide, iron oxide and chromium oxide can be added as the coloring agent(s). For example, in the case where the sintered body manufactured from the composition and the calcined body is used as the dental material, it is preferred in the first layer that a content rate of erbium oxide is from 0.08 mass % to 0.37 mass %, a content rate of iron oxide is from 0.08 mass % to 0.15 mass % and a content rate of chromium oxide is from 0.0008 mass % to 0.0012 mass %, relative to the total mass of the zirconia and the stabilizing agent(s). It is preferred in the second layer that a content rate of erbium oxide is from 0.06 mass % to 0.42 mass %, a content rate of iron oxide is from 0.06 mass % to 0.18 mass % and a content rate of chromium oxide is from 0.0006 mass % to 0.001 mass %, relative to the total mass of the zirconia and the stabilizing agent(s). It is preferred in the third layer that a content rate of erbium oxide is from 0.06 mass % to 0.17 mass %, a content rate of iron oxide is from 0.018 mass % to 0.042 mass % and a content rate of chromium oxide is from 0.0001 mass % to 0.0003 mass %, relative to the total mass of the zirconia and the stabilizing agent(s). It is preferred in the fourth layer that a content rate of erbium oxide is from 0 mass % to 0.12 mass %, a content rate of iron oxide is from 0 mass % to 0.001 mass % and a content rate of chromium oxide is from 0 mass % to 0.0001 mass %, relative to the total mass of the zirconia and the stabilizing agent(s). It is preferred that the content rates of erbium oxide, iron oxide and chromium oxide decrease from the first layer to the fourth layer, in turn.

For example, in the case where the sintered body manufactured from the composition and the calcined body is used as the dental material, it is preferred in the first layer that a content rate of erbium oxide is from 0.08 mass % to 2.2 mass %, a content rate of iron oxide is from 0.003 mass % to 0.12 mass % and a content rate of praseodymium oxide is from 0.003 mass % to 0.12 mass %, relative to the total mass of the zirconia and the stabilizing agent(s). It is preferred in the second layer that a content rate of erbium oxide is from 0.06 mass % to 1.9 mass %, a content rate of iron oxide is from 0.002 mass % to 0.11 mass % and a content rate of praseodymium oxide is from 0.002 mass % to 0.11 mass %, relative to the total mass of the zirconia and the stabilizing agent(s). It is preferred in the third layer that a content rate of erbium oxide is from 0.018 mass % to 1 mass %, a content rate of iron oxide is from 0.008 mass % to 0.06 mass % and a content rate of praseodymium oxide is from 0.0008 mass % to 0.06 mass %, relative to the total mass of the zirconia and the stabilizing agent(s). It is preferred in the fourth layer that a content rate of erbium oxide is from 0 mass % to 0.7 mass %, a content rate of iron oxide is from 0 mass % to 0.05 mass % and a content rate of praseodymium oxide is from 0 mass % to 0.05 mass %, relative to the total mass of the zirconia and the stabilizing agent(s). It is preferred that the content rates of erbium oxide, iron oxide and praseodymium oxide decrease from the first layer to the fourth layer, in turn.

The content rate of coloring agent(s) can be calculated theoretically based on an adding amount to the total mass of zirconia and the stabilizing agent(s) and the manufacturing method.

A powdery (or granular, collectively termed as "powdery" herein) material, a fluid in which the powdery material is added to a solvent and a compact (or shaped body) made by shaping the powdery material to a predetermined form may be also included in the composition of the present disclosure. That is, the composition may be a powder, paste or wet composition (i.e., it may be present in a solvent or may include a solvent). The composition may include an additive agent(s) such as a binder, coloring agent(s) etc. In addition, a mass of the additive agent(s) such as a solvent, a binder etc. is not taken into consideration in calculation of the above content rate.

If the composition of the present disclosure is a compact, the compact may be formed by any shaping (or compacting) method and may be formed by press molding, injection molding, and stereolithography, for example. The compact of the present disclosure may be also formed by multi-step processing. CIP (Cold Isostatic Pressing) may be further applied to the composition of the present disclosure after the press molding, for example.

The calcined body of the present disclosure may be obtained by burning (or heating) the composition of the present disclosure at a temperature ranging from 800 degrees Celsius to 1200 degrees Celsius under atmospheric pressure.

The calcined body of the present disclosure may be turned to the zirconia sintered body of the present disclosure by being burned at a temperature ranging from 1350 degrees Celsius to 1600 degrees Celsius under atmospheric pressure.

It is preferred that a length (thickness) of a lamination direction of the composition and the calcined body is determined such that a target length of the sintered body is realized in consideration of sintering contraction. For example, in the case where the length of the sintered body in the lamination direction is intended to be from 5 mm to 18 mm, the length (thickness) in the lamination direction of the composition and the calcined body can be set as in a range from 10 mm to 26 mm.

Next, an exemplary example of a manufacturing method for a composition, a calcined body and a sintered body of the present disclosure will be explained.

First, zirconia and a stabilizing agent are mixed in water in a wet process to form a slurry. Next, the slurry is dried to be formed in a grain form. Next, the granulated substance is calcined to produce a primary powder.

Next, the primary powder is divided into the number of the layers in an intended lamination. For example, in case of producing the above-mentioned composition and calcined body having total four layers, the primary powder is divided into four parts and referred to as first to fourth powders, respectively. A coloring agent(s) is added to each powder. An addition amount of the coloring agent(s) is suitably adjusted so that the color of each layer is expressed. And in each powder, zirconia is pulverized and mixed in water until zirconia has a desired size, and a zirconia slurry is formed. Next, the slurry is dried and granulated to produce a secondary powder of each layer. When adding the additive agent(s), such as an aluminum oxide, titanium oxide, a binder, etc., such additive agent(s) may be added at a time of the production of the primary powder or at a time of the production of the secondary powder.

Next, a plurality of the powders is laminated in order. Before laminating an upper layer, an upper surface of a lower layer is smoothed evenly, without applying press processing. For example, the upper surface of the lower layer powder is leveled to make the upper surface flat. For example, in case of producing the above-mentioned composition and calcined body having a total of four layers, the mold is charged with the first powder to a predetermined thickness (for example, from 25% to 45% of the whole thickness). At this time, the upper surface of the first powder is leveled without applying the press processing. Next, the second powder is put on the first powder to a predetermined thickness (for example, from 5% to 25% of the whole thickness). An upper surface of the second layer is also leveled without applying the press processing. The third powder is put on the second powder to a predetermined thickness (for example, from 5% to 25% of the whole thickness). An upper surface of the third layer is also leveled without applying the press processing. Next, the fourth powder is put on the third powder to a predetermined thickness (for example, from 25% to 45% of the whole thickness). An upper surface of the fourth layer is also leveled without applying the press processing. It is preferred that these powders are laminated so that a content rate of color agent(s) may increase or decrease in order from the first layer to the fourth layer.

By not applying the press processing before putting the following layer, an adhesion between adjoining layers can be improved in the sintered body. Accordingly, the strength can be enhanced. Furthermore, a difference in color between adjoining layers can be relaxed. Thereby, in the sintered body, a color can be naturally changed in the lamination direction (a gradation can be made).

In addition, according to this method, an intermediate layer(s) is not needed between respective main layers. Namely, only four layers are to be laminated, in case of laminating four main layers. Moreover, the press processing is not needed for each layer. Accordingly, time and effort can be greatly saved, and a manufacturing cost can be reduced.

Next, after all the layers are laminated, a press-forming (molding) is performed, and a compact (molded product) as a composition of the present disclosure is produced.

In the case of not producing the calcined body, by burning (heating) the composition at a temperature ranging from 1400 degrees Celsius to 1600 degrees Celsius, preferably from 1450 degrees Celsius to 1550 degrees Celsius, the zirconia powder is subjected to sinter, so that the zirconia sintered body of the present disclosure is produced. A desired shape may be formed (molded) at a stage of a molded product (compact).

In the case of producing the calcined body, the calcined body is produced by burning (heating) the composition at a temperature ranging from 800 degrees Celsius to 1200 degrees Celsius. Next, by burning the calcined body at a temperature ranging from 1400 degrees Celsius to 1600 degrees Celsius, preferably from 1450 degrees Celsius to 1550 degrees Celsius, the zirconia powder is subjected to sinter, so that the zirconia sintered body of the present disclosure is produced. A shaping (forming) may be carried out by machining etc. at the stage of the calcined body or may be carried out after sintering. The shaping (forming) can be carried out by a CAD/CAM system.

The production method of the dental prosthesis is the same as the above-mentioned production method of the sintered body except shaping (forming) the calcined body or the sintered body in tooth crown shape.

In addition, in the above-mentioned embodiment, although the composition, the calcined body and the sintered body based on the laminated body of four layers are illustrated, it is not limited to four layers. For example, it may be a composition, a calcined body and a sintered body produced from the laminated body having two layers of the above first layer and fourth layer. Alternatively, it may be a composition, a calcined body and a sintered body produced from the laminated body having three layers of the above first layer, the second layer and the fourth layer, or the above first layer, the third layer and the fourth layer. Moreover, FIG. 1 is intended to easily explain a spatial relationship and a direction among respective points, and a form and a size are not limited to the embodiment shown in FIG. 1.

EXAMPLES

Examples 1 to 10

Zirconia sintered bodies in which a content rate of coloring agent(s) differ in stages were produced, and a chromaticity of each zirconia sintered body was measured.

First, a zirconia powder(s) containing a stabilizing agent(s) was produced. Yttria of 7.2 mass % as the stabilizing agent was added to the zirconia powder of 92.8 mass %. To a mixed powder of zirconia and yttria (100 mass %), an alumina sol was added so as to add alumina of 0.1 mass %, and further water of 200 mass %, an antifoaming agent of 0.2 mass % and a dispersing agent of 1 mass % were added to the mixed powder of zirconia and yttria (100 mass %), and this mixture was pulverized by a ball mill for 20 hours. A mean particle size of a slurry made after the pulverization was 0.12 µm. Next, it was granulated with a spray drier, the produced granule was fired at 950 degrees Celsius for 2 hours to produce a primary powder.

Next, the primary powder was divided into four. Respective powders were referred to as a first, a second, a third and a fourth powders. In Examples 1 to 10, coloring agents shown in the following Tables 1 to 10 were added to respective powders. Values shown in Tables are additive rates to the mixed powder of zirconia and yttria (100 mass %). In addition, a titania of 0.2 mass %, water of 200 mass %, an antifoaming agent of 0.2 mass % and a dispersing agent of 1 mass % to the mixed powder of zirconia and yttria (100 mass %) were added to respective powders, and this mixture was pulverized by the ball mill for 15 hours. A mean particle size of a slurry made after the pulverization was 0.13 µm. Next, a binder of 0.2 mass % and a release agent of 0.2 mass % are added thereto, mixed with the ball mill for 15 hours. Next, the produced slurries were granulated with a spray drier, and secondary powders as the first, the second, the third and the fourth powders were produced.

Next, a compact (molded product) was produced. A metallic mold with an inner dimension of 82 mm×25 mm was charged with 35 g of the first powder, and an upper surface of the first powder was evenly smoothed by leveling the upper surface. Next, 15 g of the second powder was put onto the first powder, and an upper surface of the second powder was evenly smoothed by leveling the upper surface. Next, 15 g of the third powder was put onto the second powder, and an upper surface of the third powder was evenly smoothed by leveling the upper surface. Next, 35 g of the fourth powder was put onto the third powder, and an upper surface of the fourth powder was evenly smoothed by leveling the upper surface. Next, an upper die was set and a primary press-forming (molding) was performed at a surface pressure 300 kg/cm$^2$ for 90 seconds with a one-axis press-forming machine. Next, a CIP pressing of the primary press-forming body was carried out for 5 minutes at 1700 kg/cm$^2$, and a compact (molded product) was produced.

Next, the compact (molded product) was fired at 1000 degrees Celsius for 2 hours to produce a calcined body. Next, the calcined body was shaped into tooth crown shape using the CAD/CAM system (Katana system, the Kuraray Noritake Dental Inc.). Next, the calcined body was fired at 1500 degrees Celsius for 2 hours to produce a sintered body. The sintered body had a length of 8 mm in a lamination direction from the first powder to the fourth powder of the sintered body.

In any sintered body of Examples 1 to 10, a gradation which changes from light-yellow to whity-yellow color was formed toward a region corresponding to the fourth layer from a region corresponding to the first layer of the composition, and a similar appearance to a natural tooth was presented.

TABLE 1

| Example 1 | Erbium oxide/ mass % | Iron oxide/ mass % | Praseodymium oxide/ mass % | Chromium oxide/ mass % |
|---|---|---|---|---|
| Fourth powder | 0 | 0 | 0 | 0 |
| Third powder | 0.02 | 0.04 | 0 | 0.0002 |
| Second powder | 0.08 | 0.16 | 0 | 0.0008 |
| First powder | 0.10 | 0.20 | 0 | 0.0010 |

TABLE 2

| Example 2 | Erbium oxide/ mass % | Iron oxide/ mass % | Praseodymium oxide/ mass % | Chromium oxide/ mass % |
|---|---|---|---|---|
| Fourth powder | 0 | 0 | 0 | 0 |
| Third powder | 0.1 | 0.02 | 0 | 0.0002 |
| Second powder | 0.4 | 0.08 | 0 | 0.0008 |
| First powder | 0.5 | 0.10 | 0 | 0.0010 |

TABLE 3

| Example 3 | Erbium oxide/ mass % | Iron oxide/ mass % | Praseodymium oxide/ mass % | Chromium oxide/ mass % |
|---|---|---|---|---|
| Fourth powder | 0.10 | 0 | 0 | 0 |
| Third powder | 0.15 | 0.026 | 0 | 0.0002 |
| Second powder | 0.30 | 0.104 | 0 | 0.0008 |
| First powder | 0.35 | 0.130 | 0 | 0.0010 |

TABLE 4

| Example 4 | Erbium oxide/ mass % | Iron oxide/ mass % | Praseodymium oxide/ mass % | Chromium oxide/ mass % |
|---|---|---|---|---|
| Fourth powder | 0.15 | 0.05 | 0 | 0 |
| Third powder | 0.22 | 0.06 | 0 | 0 |
| Second powder | 0.43 | 0.09 | 0 | 0 |
| First powder | 0.50 | 0.10 | 0 | 0 |

TABLE 5

| Example 5 | Erbium oxide/ mass % | Iron oxide/ mass % | Praseodymium oxide/ mass % | Chromium oxide/ mass % |
|---|---|---|---|---|
| Fourth powder | 0.15 | 0.050 | 0 | 0 |
| Third powder | 0.19 | 0.066 | 0 | 0 |
| Second powder | 0.31 | 0.114 | 0 | 0 |
| First powder | 0.35 | 0.130 | 0 | 0 |

TABLE 6

| Example 6 | Erbium oxide/ mass % | Iron oxide/ mass % | Praseodymium oxide/ mass % | Chromium oxide/ mass % |
|---|---|---|---|---|
| Fourth powder | 0 | 0 | 0 | 0 |
| Third powder | 0.07 | 0.014 | 0 | 0 |
| Second powder | 0.28 | 0.056 | 0 | 0 |
| First powder | 0.35 | 0.070 | 0 | 0 |

TABLE 7

| Example 7 | Erbium oxide/ mass % | Iron oxide/ mass % | Praseodymium oxide/ mass % | Chromium oxide/ mass % |
|---|---|---|---|---|
| Fourth powder | 0.10 | 0.005 | 0.005 | 0 |
| Third powder | 0.48 | 0.024 | 0.024 | 0 |
| Second powder | 1.62 | 0.081 | 0.081 | 0 |
| First powder | 2.00 | 0.100 | 0.100 | 0 |

TABLE 8

| Example 8 | Erbium oxide/ mass % | Iron oxide/ mass % | Praseodymium oxide/ mass % | Chromium oxide/ mass % |
|---|---|---|---|---|
| Fourth powder | 0.10 | 0.005 | 0 | 0 |
| Third powder | 0.15 | 0.030 | 0.001 | 0 |
| Second powder | 0.30 | 0.105 | 0.004 | 0 |
| First powder | 0.35 | 0.130 | 0.005 | 0 |

TABLE 9

| Example 9 | Erbium oxide/ mass % | Iron oxide/ mass % | Praseodymium oxide/ mass % | Chromium oxide/ mass % |
|---|---|---|---|---|
| Fourth powder | 0 | 0 | 0 | 0 |
| Third powder | 0.02 | 0.001 | 0.001 | 0 |

TABLE 9-continued

| Example 9 | Erbium oxide/ mass % | Iron oxide/ mass % | Praseodymium oxide/ mass % | Chromium oxide/ mass % |
|---|---|---|---|---|
| Second powder | 0.08 | 0.004 | 0.004 | 0 |
| First powder | 0.10 | 0.005 | 0.005 | 0 |

TABLE 10

| Example 10 | Erbium oxide/ mass % | Iron oxide/ mass % | Praseodymium oxide/ mass % | Chromium oxide/ mass % |
|---|---|---|---|---|
| Fourth powder | 0.5 | 0.025 | 0.025 | 0 |
| Third powder | 0.8 | 0.040 | 0.040 | 0 |
| Second powder | 1.7 | 0.085 | 0.085 | 0 |
| First powder | 2.0 | 0.100 | 0.100 | 0 |

Then, as to the first power, the second power, the third power and the fourth power, independent sintered bodies were produced, respectively and a chromaticity by an L*a*b* colorimetric system for each body was measured. The chromaticity was measured using a measuring device CE100-DC/US made by Olympus Corporation, after processing the sintered bodies into disks (14 mm in diameter and 1.2 mm in thickness) and grinding both sides of disks. In addition, based on the measurement results of the chromaticity, color differences $\Delta E^*ab_{1-3}$ between adjoining layers were calculated. Furthermore, a color difference $\Delta E^*ab_4$ between the first layer and the fourth layer was calculated. And, $(\Delta E^*ab_1+\Delta E^*ab_2+\Delta E^*ab_3)-\Delta E^*ab_4$ was calculated. Each chromaticity is shown in Tables 11-20. Each color difference is shown in Tables 21-22.

It is thought that the chromaticity of each powder expresses the chromaticity of each point of the zirconia sintered bodies produced from the laminated body of a plurality of the powders. A combination of four sintered bodies of Example 9 presented a bright color as a whole. A combination of four sintered bodies of Example 10 presented a dark color as a whole.

In the sintered bodies of the first layer, L* was a range from 58 to 76, a* was a range from −2 to 8, and b* was a range from 5 to 27. In the sintered bodies of the second layer, L* was a range from 66 to 81, a* was a range from −2 to 6, and b* was a range from 4 to 21. In the sintered bodies of the third layer, L* was a range from 69 to 83, a* was a range from −2 to 2, and b* was a range from 3 to 17. In the sintered bodies of the fourth layer, L* was a range from 71 to 84, a* was a range from −2 to 1, and b* was a range from 2 to 15.

The color differences between the sintered body of the first layer and the sintered body of the second layer ranged from 3 to 15. The color differences between the sintered body of the second layer and the sintered body of the third layer ranged from 1 to 11. The color differences between the sintered body of the third layer and the sintered body of the fourth layer ranged from 1 to 4. There was a tendency that the color differences between adjoining layers become small in a direction from the first layer toward the fourth layer. In addition, the color differences between the sintered body of the first layer and the sintered body of the fourth layer ranged from 8 to 29. Values which result from by deducting the color difference between the sintered body of the first layer and the sintered body of the fourth layer from a sum total of the color difference between the sintered body of the first layer and the sintered body of the second layer, the color difference between the sintered body of the second layer and the sintered body of the third layer, and the color difference between the sintered body of the third layer and the sintered body of the fourth layer were less than 1.

TABLE 11

| Example 1 | L* | a* | b* |
|---|---|---|---|
| Sintered body of fourth powder | 71.97 | 0.60 | 2.10 |
| Sintered body of third powder | 70.36 | 0.61 | 4.44 |
| Sintered body of second powder | 68.77 | 0.82 | 11.22 |
| Sintered body of first powder | 64.79 | 0.93 | 19.76 |

TABLE 12

| Example 2 | L* | a* | b* |
|---|---|---|---|
| Sintered body of fourth powder | 74.33 | −0.75 | 5.24 |
| Sintered body of third powder | 73.72 | −0.63 | 6.35 |
| Sintered body of second powder | 73.11 | 1.70 | 9.59 |
| Sintered body of first powder | 71.59 | 2.92 | 13.65 |

TABLE 13

| Example 3 | L* | a* | b* |
|---|---|---|---|
| Sintered body of fourth powder | 71.97 | 0.60 | 2.10 |
| Sintered body of third powder | 71.38 | 0.64 | 3.68 |
| Sintered body of second powder | 70.80 | 1.37 | 8.27 |
| Sintered body of first powder | 69.35 | 1.76 | 14.04 |

TABLE 14

| Example 4 | L* | a* | b* |
|---|---|---|---|
| Sintered body of fourth powder | 73.79 | −0.90 | 6.64 |
| Sintered body of third powder | 73.30 | −0.78 | 7.57 |
| Sintered body of second powder | 72.81 | 1.65 | 10.26 |
| Sintered body of first powder | 71.59 | 2.92 | 13.65 |

TABLE 15

| Example 5 | L* | a* | b* |
|---|---|---|---|
| Sintered body of fourth powder | 73.79 | −0.90 | 6.64 |
| Sintered body of third powder | 72.80 | −0.82 | 7.62 |

TABLE 15-continued

| Example 5 | L* | a* | b* |
|---|---|---|---|
| Sintered body of second powder | 71.81 | 0.88 | 10.46 |
| Sintered body of first powder | 69.35 | 1.76 | 14.04 |

TABLE 16

| Example 6 | L* | a* | b* |
|---|---|---|---|
| Sintered body of fourth powder | 83.97 | −1.89 | 4.17 |
| Sintered body of third powder | 81.18 | −1.78 | 5.04 |
| Sintered body of second powder | 78.42 | 0.37 | 7.57 |
| Sintered body of first powder | 71.52 | 1.49 | 10.75 |

TABLE 17

| Example 7 | L* | a* | b* |
|---|---|---|---|
| Sintered body of fourth powder | 75.77 | −1.41 | 5.70 |
| Sintered body of third powder | 71.82 | −1.13 | 8.40 |
| Sintered body of second powder | 67.92 | 4.47 | 16.24 |
| Sintered body of first powder | 58.16 | 7.40 | 26.1 |

TABLE 18

| Example 8 | L* | a* | b* |
|---|---|---|---|
| Sintered body of fourth powder | 75.77 | −1.41 | 5.70 |
| Sintered body of third powder | 74.33 | −1.31 | 6.80 |
| Sintered body of second powder | 72.91 | 0.71 | 10.01 |
| Sintered body of first powder | 69.35 | 1.76 | 14.04 |

TABLE 19

| Example 9 | L* | a* | b* |
|---|---|---|---|
| Sintered body of fourth powder | 83.97 | −1.89 | 4.17 |
| Sintered body of third powder | 82.13 | −1.87 | 4.37 |
| Sintered body of second powder | 80.31 | −1.57 | 4.96 |
| Sintered body of first powder | 75.77 | −1.41 | 5.70 |

TABLE 20

| Example 10 | L* | a* | b* |
|---|---|---|---|
| Sintered body of fourth powder | 72.49 | 0.97 | 14.5 |
| Sintered body of third powder | 69.28 | 1.18 | 16.03 |

TABLE 20-continued

| Example 10 | L* | a* | b* |
|---|---|---|---|
| Sintered body of second powder | 66.10 | 5.26 | 20.49 |
| Sintered body of first powder | 58.16 | 7.40 | 26.10 |

TABLE 21

| Example | 1 | 2 | 3 | 4 | 5 |
|---|---|---|---|---|---|
| Color difference $\Delta E^*ab_1$ between third powder and fourth powder | 2.8 | 1.3 | 1.7 | 1.1 | 1.4 |
| Color difference $\Delta E^*ab_2$ between second powder and third powder | 7.0 | 4.0 | 4.7 | 3.7 | 3.5 |
| Color difference $\Delta E^*ab_3$ between first powder and second powder | 9.4 | 4.5 | 6.0 | 3.8 | 4.4 |
| Color difference $\Delta E^*ab_4$ between first powder and fourth powder | 19.1 | 9.6 | 12.3 | 8.3 | 9.0 |
| $(\Delta E^*ab_1 + \Delta E^*ab_2 + \Delta E^*ab_3) - \Delta E^*ab_4$ | 0.1 | 0.2 | 0.1 | 0.3 | 0.3 |

TABLE 22

| Example | 6 | 7 | 8 | 9 | 10 |
|---|---|---|---|---|---|
| Color difference $\Delta E^*ab_1$ between third powder and fourth powder | 2.9 | 4.8 | 1.8 | 1.9 | 3.6 |
| Color difference $\Delta E^*ab_2$ between second powder and third powder | 4.3 | 10.4 | 4.0 | 1.9 | 6.8 |
| Color difference $\Delta E^*ab_3$ between first powder and second powder | 7.7 | 14.2 | 5.5 | 4.6 | 10.0 |
| Color difference $\Delta E^*ab_4$ between first powder and fourth powder | 14.5 | 28.4 | 11.0 | 8.4 | 19.5 |
| $(\Delta E^*ab_1 + \Delta E^*ab_2 + \Delta E^*ab_3) - \Delta E^*ab_4$ | 0.4 | 1.0 | 0.3 | 0 | 0.9 |

As to the first powder, the second powder, the third powder and the fourth powder in Example 4, independent zirconia sintered bodies were produced, respectively, and values of flexural strength, values of fracture toughness and the peak ratios of the monoclinic system after hydrothermal test were measured. Measurement results are shown in Table 23. The values of the flexural strength of the zirconia sintered body were measured in conformity with JISR1601. The values of the fracture toughness of the zirconia sintered body were measured in conformity with JISR1607. A hydrothermal test was in conformity with ISO13356 under a condition of 180 degrees Celsius, 1 MPa and 5 hours. After applying the hydrothermal test, X-ray diffraction patterns of the zirconia sintered bodies were measured with the CuKα rays, and the peak ratios of the monoclinic system, i.e., degrees of the phase transition to the monoclinic by the hydrothermal test were measured. The values of the flexural strength were 1200 MPa or more, the values of the fracture toughness were 4 MPa·m$^{1/2}$ or more, and also the peak ratios of the monoclinic system were 1 or less for any sintered bodies. Since the compositions of the zirconia sintered bodies in other Examples are also the similar, it is thought that the similar results would be obtained.

TABLE 23

| Measurement sample | Flexural strength/ MPa | Fracture toughness/ MPa·√m | Peak ratio of monoclinic system* |
|---|---|---|---|
| Sintered body of first powder | 1210 | 4.3 | 0.58 |
| Sintered body of second powder | 1216 | 4.3 | 0.59 |

TABLE 23-continued

| Measurement sample | Flexural strength/ MPa | Fracture toughness/ MPa·√m | Peak ratio of monoclinic system* |
|---|---|---|---|
| Sintered body of third powder | 1204 | 4.3 | 0.60 |
| Sintered body of fourth powder | 1202 | 4.3 | 0.59 |

A value of the flexural strength of the sintered body in which the first powder to the fourth powder of Example 4 were laminated was measured. The flexural strengths were measured on the calcined body and the sintered body. As a comparative example, a value of flexural strength of a sintered body produced from a composition in which a press treatment was applied at every time of charging with each powder was also measured. Test pieces were cut out such that the longitudinal direction corresponds to the lamination direction. As shown in FIG. 2, in the test piece, a boundary between the second powder and the third powder was located at the center of the test piece. A load point of a three-point bending test was consistent with a position of the boundary. Measurement results are shown in Table 24.

Compared to the calcined body and sintered body to which the press treatment was applied at every time of charging with the powder of respective layers, the flexural strength of the calcined body and sintered body to which the press treatment was not applied was able to be enhanced. In addition, a boundary surface (interface) of the laminated layers was destroyed in the calcined body and the sintered body to which the press treatment was applied; on the other hand, the calcined body and the sintered body to which the press treatment was not applied was destroyed near a boundary region and the destroy was not restricted to the boundary surface. Accordingly, rather in the case where the press treatment was not applied, it was recognized that a junction between layers can be improved. Since the compositions of the zirconia sintered body in other Examples is also similar to one another, it is thought that the similar results would be obtained.

TABLE 24

| Measurement sample | Flexural strength of calcined body/ MPa | Flexural strength of sintered body/ MPa |
|---|---|---|
| Example (without press treatment) | 36 | 1080 |
| Comparative Example (with press treatment) | 31 | 1011 |

Although the zirconia sintered body of the prevent disclosure, and the composition and the calcined body for the zirconia sintered body are explained based on the above embodiments and Examples, the present disclosure is not limited to the above embodiments and Examples, and may include any modification, change and improvement to the a variety of disclosed elements based on the basic technical idea within the scope of the present disclosure (including each element in the claims, embodiments and Examples in description and drawings). Within the scope of the present disclosure, various combinations, replacements or substitutions and selections of a variety of disclosed elements (including each element in the claims, embodiments and Examples in description and drawings) are available.

A further problem, object and embodiment of the present disclosure will become apparent also from the entire disclosure of the present disclosure including the claims, description and drawings.

As to the numerical range disclosed in the present description, it should be interpreted that arbitrary numerical values or smaller ranges included in the range concerned is indicated concretely even if there is no explicit description(s).

INDUSTRIAL APPLICABILITY

The zirconia sintered body of the present disclosure is applicable to various uses for dental materials such as a prosthesis, connectors for optical fibers such as a ferrule and sleeve, various tools (crusher balls, grinding tools, for example), various parts (screws, bolts and nuts, for example), various sensors, components for electronics, and accessories (straps for watch, for example). In the case where the zirconia sintered body is used as the dental material, it can be used for a coping, a framework, a crown, a crown bridge, an abutment, an implant, an implant screw, an implant fixture, an implant bridge, an implant bar, a bracket, a baseplate, an inlay, an onlay, an orthotic wire, laminate veneer, etc.

REFERENCE SIGNS LIST

10 Zirconia sintered body
A First point
B Second point
C Third point
D Fourth point
P One end
Q Other end
X First direction
Y Second direction

What is claimed is:

1. A zirconia sintered body,
wherein, on a straight line extending in a first direction from one end to the other end,
when a chromaticity ($L^*$, $a^*$, $b^*$) by a $L^*a^*b^*$ colorimetric system of a first point positioned in a section from said one end to 25% of a whole length is ($L1$, $a1$, $b1$) and a chromaticity ($L^*$, $a^*$, $b^*$) by the $L^*a^*b^*$ colorimetric system of a second point positioned in a section from said other end to 25% of the whole length, is ($L2$, $a2$, $b2$),
L1 ranges from 58.0 to 76.0,
a1 ranges from −1.6 to 7.6,
b1 ranges from 5.5 to 26.3,
L2 ranges from 71.8 to 84.2,
a2 ranges from −2.1 to 1.8,
b2 ranges from 1.9 to 16.0,
L1<L2,
a1>a2,
b1>b2, and
a tendency to increase or decrease the chromaticity by the $L^*a^*b^*$ colorimetric system from said first point to said second point does not change.

2. The zirconia sintered body according to claim 1,
wherein, on a straight line connecting said first point and said second point,
there is no section where the $L^*$ value decreases by 1 or more from said first point toward said second point,
there is no section where the $a^*$ value increases by 1 or more from said first point toward said second point, and
there is no section where the $b^*$ value increases by 1 or more from said first point toward said second point.

3. The zirconia sintered body according to claim 1,
wherein, on the straight line connecting said first point to said second point, when a chromaticity (L*, a*, b*) by the L*a*b* colorimetric system of a third point between said first point and said second point is (L3, a3, b3),
L3 ranges from 65.9 to 80.5,
a3 ranges from −1.8 to 5.5,
b3 ranges from 4.8 to 20.7,
L1<L3<L2,
a1>a3>a2, and
b1>b3>b2.

4. The zirconia sintered body according to claim 3,
wherein, on the straight line connecting said first point to said second point,
when a chromaticity (L*, a*, b*) by the L*a*b* colorimetric system of a forth point between said third point and said second point is (L4, a4, b4),
L4 ranges from 69.1 to 82.3,
a4 ranges from −2.1 to 1.4,
b4 ranges from 3.5 to 16.2,
L1<L3<L4<L2,
a1>a3>a4>a2, and
b1>b3>b4>b2.

5. The zirconia sintered body according to claim 4, wherein said third point is placed at a distance of 45% of the whole length from said one end, and
said fourth point is placed at a distance of 55% of the whole length from said one end.

6. The zirconia sintered body according to claim 4,
wherein, with respect to said first point, said third point, said fourth point and said second point,
when a difference in the L* value between adjacent two points is ΔL*,
a difference in the a* value between adjacent two points is Δa*,
a difference in the b* value between adjacent two points is Δb* and
when ΔE*ab is calculated by the following formula 1,
ΔE*ab between said first point and said third point ranges from 3.7 to 14.3,
ΔE*ab between said third point and said fourth point ranges from 1.8 to 10.5, and
ΔE*ab between said fourth point and said second point ranges from 1.0 to 4.8

$$\Delta E^*ab = \sqrt{(\Delta L^*)^2 + (\Delta a^*)^2 + (\Delta b^*)^2} \quad \text{[Formula 1]}.$$

7. The zirconia sintered body according to claim 1,
wherein, on the straight line connecting said first point to said second point, when a chromaticity (L*, a*, b*) by the L*a*b* colorimetric system of a third point between said first point and said second point is (L3, a3, b3),
L3 ranges from 69.1 to 82.3,
a3 ranges from −2.1 to 1.4,
b3 ranges from 3.5 to 16.2,
L1<L3<L2,
a1>a3>a2, and
b1>b3>b2.

8. A zirconia sintered body,
wherein, color changes in a first direction from one end toward the other end, and
a tendency to increase or decrease the chromaticity by the L*a*b* colorimetric system on a straight line from said one end to the other end does not change.

9. The zirconia sintered body according to claim 8,
wherein, on the straight line connecting said one end and said other end, there are a tendency of increasing L* value and a tendency of decreasing a* value and b* value, from said first point toward said second point.

10. The zirconia sintered body according to claim 1,
wherein a distance from said one end to said other end ranges from 5 mm to 18 mm.

11. The zirconia sintered body according to claim 1,
wherein there is no change of a color along a second direction perpendicular to said first direction.

12. The zirconia sintered body according to claim 11,
wherein, on two points on a straight line extending in said second direction,
when a difference in the L* value between said two points is ΔL*,
a difference in the a* value between said two points is Δa*,
a difference in the b* value between said two points is Δb* and
when ΔE*ab is calculated by the following formula 2
ΔE*ab is less than 1

$$\Delta E^*ab = \sqrt{(\Delta L^*)^2 + (\Delta a^*)^2 + (\Delta b^*)^2} \quad \text{[Formula 2]}.$$

13. The zirconia sintered body according to claim 1,
wherein a value of flexural strength measured in conformity with JISR1601 is 1000 MPa or more.

14. The zirconia sintered body according to claim 1,
wherein a value of fracture toughness measured in conformity with JISR1607 is 3.5 MPa·m$^{1/2}$ or more.

15. The zirconia sintered body according to claim 1,
wherein, in an X-ray diffraction pattern of the zirconia sintered body after applying a hydrothermal test at a temperature of 180 degrees Celsius and a pressure of 1 MPa for 5 hours, a peak ratio is 1 or less, the peak ratio being a ratio of a height of a peak existing near a position around 28° of 2θ where a monoclinic [11-1] peak appears to a height of a peak existing near a position around 30° of 2θ where a tetragonal [111] peak appears.

* * * * *